(12) United States Patent
Weiss

(10) Patent No.: US 8,993,516 B2
(45) Date of Patent: Mar. 31, 2015

(54) MEAL-TIME INSULIN ANALOGUES OF ENHANCED STABILITY

(75) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 245 days.

(21) Appl. No.: 12/937,612

(22) PCT Filed: Apr. 14, 2009

(86) PCT No.: PCT/US2009/040544
§ 371 (c)(1),
(2), (4) Date: Nov. 22, 2010

(87) PCT Pub. No.: WO2009/129250
PCT Pub. Date: Oct. 22, 2009

(65) Prior Publication Data
US 2011/0059887 A1    Mar. 10, 2011

Related U.S. Application Data

(60) Provisional application No. 61/044,532, filed on Apr. 14, 2008.

(51) Int. Cl.
A61K 38/28       (2006.01)
C07K 14/62       (2006.01)
A61K 38/00       (2006.01)

(52) U.S. Cl.
CPC ......... *C07K 14/62* (2013.01); *A61K 38/00* (2013.01)
USPC ............. 514/5.9; 514/6.2; 514/6.3; 514/6.5; 530/303

(58) Field of Classification Search
None
See application file for complete search history.

(56) References Cited

U.S. PATENT DOCUMENTS

| | | | |
|---|---|---|---|
| 5,149,716 A | 9/1992 | Vertesy et al. | |
| 5,149,777 A | 9/1992 | Hansen et al. | |
| 5,491,216 A | 2/1996 | Hoffmann et al. | |
| 5,506,202 A | 4/1996 | Vertesy et al. | |
| 5,618,913 A | 4/1997 | Brange et al. | |
| 5,698,669 A | 12/1997 | Hoffmann et al. | |
| 5,700,662 A | 12/1997 | Chance et al. | |
| 5,716,927 A | 2/1998 | Balschmidt et al. | |
| 5,977,297 A | 11/1999 | Obermeier et al. | |
| 6,011,007 A | 1/2000 | Havelund et al. | |
| 6,221,633 B1 | 4/2001 | Ertl et al. | |
| 6,268,335 B1 | 7/2001 | Brader | |
| 6,465,426 B2 | 10/2002 | Brader | |
| 6,531,448 B1 | 3/2003 | Brader | |
| 6,630,348 B1 | 10/2003 | Lee et al. | |
| 7,129,211 B2 | 10/2006 | Bhattacharya et al. | |
| 7,316,999 B2 | 1/2008 | Hoeg-Jensen et al. | |
| 7,547,821 B2 * | 6/2009 | Moloney et al. | 800/288 |
| 2001/0036916 A1 | 11/2001 | Brader | |
| 2002/0082199 A1 | 6/2002 | Brader | |
| 2003/0104981 A1 | 6/2003 | Mandic | |
| 2003/0144181 A1 | 7/2003 | Brader | |
| 2004/0014660 A1 | 1/2004 | During et al. | |
| 2004/0053816 A1 | 3/2004 | Bhattacharya et al. | |
| 2004/0214988 A1 | 10/2004 | Tirrell et al. | |
| 2005/0014679 A1 | 1/2005 | Beals et al. | |
| 2005/0039235 A1 * | 2/2005 | Moloney et al. | 800/288 |
| 2005/0176621 A1 | 8/2005 | Brader et al. | |
| 2006/0217290 A1 | 9/2006 | Kohn et al. | |
| 2007/0129284 A1 | 6/2007 | Kjeldsen et al. | |
| 2008/0146492 A1 | 6/2008 | Zimmerman et al. | |
| 2009/0304814 A1 | 12/2009 | Weiss | |
| 2010/0099601 A1 | 4/2010 | Weiss | |
| 2011/0077196 A1 | 3/2011 | Weiss | |
| 2011/0077197 A1 | 3/2011 | Habermann et al. | |
| 2011/0166064 A1 | 7/2011 | Weiss | |
| 2011/0195896 A1 | 8/2011 | Weiss et al. | |

FOREIGN PATENT DOCUMENTS

| | | |
|---|---|---|
| EP | 1090640 A2 * | 4/2001 |
| WO | 03/053339 A2 | 7/2003 |
| WO | 2005/054291 A1 | 6/2005 |

(Continued)

OTHER PUBLICATIONS

EP 07 84 3856 Supplementary European Search Report, 4 pages; Dec. 11, 2009.

Currie et al.; The influence of glucose-lowering therapies on cancer risk in type 2 diabetes; Diabetologia; 52(9); pp. 1766-1777; Sep. 2009.

Hemkens et al.; Risk of malignancies in patients with diabetes treated with human insulin or insulin analogues: a cohort study; Diabetologia 52(9); pp. 1732-1744; Sep. 2009.

Tuffs; German agency suspects that insulin analogue glargine increases risk of cancer; PubMed; BMJ; 339:b2774; 1 page (no abstract available); Jul. 8, 2009.

Shukla et al.; Analysis of signaling pathways related to cell proliferation stimulated by insulin analogs in human mammary epithelial cell lines; Endrocine-Related Cancer; 16(2); pp. 429-441; Jun. 2009.

(Continued)

*Primary Examiner* — Gyan Chandra
(74) *Attorney, Agent, or Firm* — Hahn Loeser & Parks LLP

(57) ABSTRACT

A method treating a patient includes administering a physiologically effective amount of a fibrillation-resistant insulin analogue or a physiologically acceptable salt thereof to the patient. The fibrillation-resistant insulin analogue or a physiologically acceptable salt thereof, contains an insulin A-chain sequence modified at position A8 and an insulin B-chain sequence or an analogue thereof. The fibrillation-resistant insulin analogue may exhibit thermodynamic stability similar to or exceeding that of wild-type human insulin and displays a susceptibility to fibrillation similar to or exceeding that of wild-type human insulin. An insulin analogue may display greater in vitro insulin receptor binding than normal insulin while displaying binding to IGFR less than twice that of normal insulin and less than that of fast-acting insulin analogs. The fibrillation-resistant insulin may be used to treat a patient by subcutaneous injection or by using an implantable or external insulin pump, due to its fibrillation resistance.

11 Claims, 8 Drawing Sheets

(56) References Cited

FOREIGN PATENT DOCUMENTS

| | | | |
|---|---|---|---|
| WO | 2007/081824 A2 | 7/2007 |
| WO | 2007/096332 A1 | 8/2007 |
| WO | 2007/081824 A3 | 2/2008 |
| WO | 2008/043033 A2 | 4/2008 |
| WO | 2008/043033 A3 | 11/2008 |
| WO | 2009/087081 A2 | 7/2009 |
| WO | 2009/129250 A2 | 10/2009 |
| WO | 2009/132129 A2 | 10/2009 |
| WO | 2010/132129 A3 | 1/2010 |
| WO | 2009/129250 A3 | 2/2010 |
| WO | 2010/014946 A2 | 2/2010 |
| WO | 2010/014946 A3 | 5/2010 |
| WO | 2011/028813 A2 | 3/2011 |
| WO | 2011/072288 A2 | 6/2011 |
| WO | 2011/103575 A1 | 8/2011 |

OTHER PUBLICATIONS

Rajpal et al.; Single-Chain Insulins as Receptor Agonists; The Endrocrine Society; 27 pages; Feb. 19, 2009.
Weinstein, et al.; Insulin analogues display IGF-I-like mitogenic and anti-apoptotic activities in cultured cancer cells; Diabetes/Metabolism Research and Reviews; 25(1); pp. 41-49; Jan. 2009.
Zelobowska et al.; Mitogenic potency of insulin glargine; Polish Journal of Endocrinology; vol. 60, No. 1; pp. 34-39; 2009.
Hua et al.; Design of an Active Ultrastable Single-chain Insulin Analog; The Journal of Biological Chemistry; vol. 283, No. 21; pp. 14703-14716; May 23, 2008.
Liefvendahl et al.; Mitogenic effect of the insulin analogue glargine in malignant cells in comparison with insulin and IGF-I; PubMed; 1 page (abstract only); Apr. 7, 2008.
Du et al.; Insulin analogs with B24 or B25 phenylalanine replaced by biphenylalanine; Acta Biochem Biophys Sin; vol. 40, No. 2; pp. 133-139; Feb. 2008.
Mayer et al.; Proliferative effects of insulin analogues on mammary epithelial cells; Archives of Physiology and Biochemistry; 114(1); pp. 38-44; Feb. 2008.
Kohn et al.; pl-shifted insulin analogs with extended in vivo time action and favorable receptor selectivity; PubMed; 28 (4); 1 page (abstract only); Jan. 25, 2007.
Nakagawa, et al.; Chiral Mutagenesis of Insulin; The Journal of Biological Chemistry; vol. 281, No. 31; pp. 22386-22396; Aug. 4, 2006.
Hua et al.; Mechanism of insulin fibrillation—The structure of insulin under amyloidogenic conditions resembles a protein-folding intermediate, Journal of Biological Chemistry; vol. 279, No. 20; pp. 21449-21460, XP002557730, ISSN 0021-9258; May 14, 2004.
Chen et al.; Sequences of B-Chain/Domain 1-10/1-9 of Insulin and Insulin-like Growth Factor 1 Determine Their Different Folding Behavior; Biochemistry; pp. 9225-9233; 2004.
Zakova et al.; Shortened Insulin Analogues: Marked Changes in Biological Activity Resulting from Replacement of TyrB26 and N-Methylation of Peptide Bonds in the C-Terminus of the B-Chain; Biochemistry; vol. 43; pp. 2323-2331; 2004.
Weiss et al.; Non-standard Insulin Design: Structure-Activity Relationships at the Periphery of the Insulin Receptor; The Journal of Molecular Biology; vol. 315; pp. 103-111; 2002.
Garriques et al.; The effect of mutations on the structure of insulin fibrils studied by Fourier transform infrared (FTIR) spectroscopy and electron microscopy; PubMed; vol. 12; 1 page (abstract only); 2002.
Weiss, et al.; Activities of Monomeric Insulin Analogs at Position A8 Are Uncorrelated with Their Thermodynamic Stabilities; The Journal of Biological Chemistry; vol. 276, No. 43; pp. 40018-40024; Oct. 26, 2001.
Nielsen et al.; Probing the Mechanism of Insulin Fibril Formation with Insulin Mutants; American Chemical Society; Biochemistry; vol. 40; pp. 8397-8409; Jun. 19, 2001.
Olsen et al.; The Relationship Between Insulin Bioactivity and Structure in the NH2-terminal A-chain Helix; Journal of Molecular Biology; vol. 284, Issue 2; pp. 477-488; Nov. 27, 1998.

Kristensen et al.; Alanine Scanning Mutagenesis of Insulin; The Journal of Biological Chemistry; vol. 272, No. 20; pp. 12978-12983; May 16, 1997.
Milazzo et al.; ASPB10 insulin induction of increased mitogenic responses and phenotypic changes in human breast epithelial cells; evidence for enhanced interations with the insulin-like growth factor-I receptor; PubMed; 18(1); 1 page (abstract only); Jan. 1997.
Doig et al.; N- and C-capping preferences for all 20 amino acids in {alpha}-helical peptides; Protein Science; vol. 4; pp. 1325-1335; 1995.
Kaarsholm et al.; Engineering Stability of the Insulin Monomer Fold with Application to Structure-Activity Relationships; Biochemistry; 32 (40); pp. 10773-10778; Oct. 1993.
Mirmira et al.; Role of the Phenylalanine B24 Side Chain in Directing Insulin Interaction with Its Receptor; The Journal of Biological Chemistry; vol. 264, No. 11; pp. 6349-6354; Apr. 15, 1989.
Zhao et al.; Design of an insulin analog with enhanced receptor binding selectivity: rationale, structure, and therapeutic implications; J. Biol. Chem. 284(46); Sep. 22, 2009; pp. 32178-32187.
Sreekanth et al.; Structural interpretation of reduced insulin activity as seen in the crystal structure of human Arg-insulin; Biochimie; 90(3); Sep. 22, 2007; pp. 467-473.
Kohn et al.; pI-shifted insulin analogs with extended in vivo time action and favorable receptor selectivity; Peptides; 28 (4); Jan. 25, 2007; pp. 935-948.
Sleiker et al.; Modifications in the B10 and B26-30 regions of the B chain of human insulin alter affinity for the human IGF-I receptor more than for the insulin receptor; Diabetologia; 40 Suppl. 2; Jul. 1997; pp. S54-S61.
Summ et al.; Binding of insulin analogs to partially purified insulin receptor from rat liver membrane (author's trans.); Hoppe Seylers Z. Physiol. Chem.; 357(5); May 1976; pp. 683-693 (Abstract only—1 page).
PCT/US2010/047546 International Search Report and Written Opinion dated May 23, 2011.
PCT/US2010/060085 International Search Report and Written Opinion dated Sep. 16, 2011.
PCT/US11/25730 International Search Report and Written Opinion dated Jul. 22, 2011.
EP 09 80 3678 Supplementary European Search Report dated Jan. 30, 2012.
Blanquart et al.; Characterization of IRA/IR hybrid insulin receptors using bioluminescence resonance energy transfer; Biochemical Pharmacology 76 (2008); Jul. 27, 2008, pp. 873-883.
Duckworth et al.; Degradation products of insulin generated by hepatocytes and by insulin protease; Journal of Biological Chemistry, vol. 263, No. 4, Apr. 6, 1988; pp. 1826-1833.
Haijuan Du et al.; Insulin analogs with B24 or B25 phenylalanine replaced by bipheylalanine; ACTA Biochimica et Biophysica Sinica, vol. 40, No. 2, 2006, pp. 133-139.
Huang et al.; Structure-Specific Effects of Protein on Cross β Assembly: Studies of Insulin Fibrillation; Biochemistry 2006, 45, Aug. 4, 2006, pp. 10278-10293, May 28, 2014.
Liu et al.; Utilization of combined chemical modification to enhance the blood-brain barrier permeability and pharmacological activity of endomorphin-a, JPET 106, 106484, Jun. 27, 2006, pp. 1-43.
Mirmira et al.; Disposition of the phenylalanine B25 side chain during insulin-receptor and insulin-insulin interactions, Biochemistry; vol. 30, No. 33; May 1, 1991; pp. 8222-8229.
Mirmira et al.; Importance of the character and configuration of residues B24 B25 and B26 in insulin-receptor interactions, Journal of Biological Chemistry, vol. 266, No. 3; Jan. 25, 1991; pp. 1428-1436.
Stemaszynska et al.; N-(2-Oxoacyl)amino Acids and Nitriles as Final Products of Dipeptide Chlorination Mediated by the Myeloperoxidase/H2O2/CI-System, European Journal of Biochemistry, vol. 92, No. 1, Sep. 25, 1978, pp. 301-308.
Wan et al,; Enhancing the Activity of Insulin at the Receptor Interface: Crystal Structure and Photo-Cross-Linking of A8 Analogues; Biochemistry 2004, 43; Nov. 25, 2004; pp. 16119-16133.
Yang et al.; An Achilles' heel in an amyloidogenic protein and its repair: insulin fibrillation and therapeutic design; J Biol Chem. Apr. 2, 2010;285(14):10806-21.

\* cited by examiner

PROINSULIN

MODEL

MEAL-TIME INSULIN ANALOGUES OF ENHANCED STABILITY

CROSS REFERENCE TO RELATED APPLICATIONS

This application claims benefit of pending U.S. Provisional Application No. 61/044,532 filed on Apr. 14, 2008.

STATEMENT REGARDING FEDERALLY SPONSORED RESEARCH OR DEVELOPMENT

This invention was made with government support under cooperative agreements awarded by the National Institutes of Health, Contract Nos. NIH R01DK069764 and R01-DK74176. The U.S. government may have certain rights to the invention.

BACKGROUND OF THE INVENTION

The stability of proteins used in medical treatment is an important concern in medicine. Protein degradation can be classified as physical or chemical degradation. Physical degradation is caused by a change in conformation that leads to aggregation of the protein and formation of protein fibrils. Chemical degradation of proteins entails a change in the pattern of covalent bonds between atoms, such as breakage or interchange of disulfide bridges, deamination or transamination of the protein.

Administration of insulin has long been established as a treatment for diabetes mellitus. Insulin is a small globular protein that plays a central role in metabolism in vertebrates. Insulin contains two chains, an A-chain, containing 21 residues, and a B-chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B-chain (residue B30) to the N-terminal residue of the A-chain (FIG. 1A). Although the structure of proinsulin has not been determined, a variety of evidence indicates that it consists of an insulin-like core and disordered connecting peptide (FIG. 1B). Formation of three specific disulfide bridges (A6-A11, A7-B7, and A20-B19; FIG. 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). Assembly and disassembly of native oligomers is thus intrinsic to the pathway of insulin biosynthesis, storage, secretion, and action.

Insulin readily misfolds in vitro to form a prototypical amyloid. Unrelated to native assembly, fibrillation is believed to occur via an amyloidogenic partial fold (FIG. 1C). Factors that accelerate or hinder fibrillation have been extensively investigated in relation to pharmaceutical formulations. Zinc-free insulin is susceptible to fibrillation under a broad range of conditions and is promoted by factors that impair native dimerization and higher-order self-assembly. A storage form of insulin in the pancreatic β-cell and in the majority of pharmaceutical formulations is believed to be stabilized by axial zinc ions coordinated by the side chains of insulin amino acids, specifically the $His^{B10}$ residues. Formulation of insulin or insulin analogues as a zinc-stabilized hexamer retards but does not prevent fibrillation, especially above room temperature and on agitation.

Amino-acid substitutions in the A- and/or B-chains of insulin have widely been investigated for possible favorable effects on the pharmacokinetics of insulin action following subcutaneous injection. Examples are known in the art of substitutions that accelerate or delay the time course of absorption. The former analogues collectively define the "meal-time" insulin analogues because patients with diabetes mellitus may inject such rapid-acting formulations at the time of a meal whereas the delayed absorption of wild-type human insulin or animal insulins (such as porcine insulin or bovine insulin) makes it necessary to inject these formulations 30-45 minutes prior to a meal. The substitutions are designed to destabilize the zinc insulin hexamer by altering the steric or electrostatic complementarity of subunit interfaces and thereby to facilitate the rapid dissociation of the zinc insulin hexamer after subcutaneous administration. A side consequence of this design is decreased chemical and physical stability of the insulin analogue formulation, which can limit the shelf life of the formulation at room temperature and cause occlusion of external insulin pumps due to formation of insulin fibrils. The present invention concerns the prevention of this increased susceptibility to fibrillation and chemical degradation by meal-time insulin analogues. In addition to patient convenience and quality of life, the rapid-acting insulin analogues may increase the safety of intensive multiple-injection regimens intended to achieve tight glycemic control. Rapid absorption is also reported to enhance the efficacy and safety of glycemic control obtained by the subcutaneous injection of an insulin analogue formulation by an external insulin pump. Despite these favorable properties, such substitutions (such as $Asp^{B28}$ in Novalog® and [$Lys^{B28}$, $Pro^{B29}$] in Humalog®) can be and often are associated with more rapid fibrillation and poorer physical stability. Similar decreases in chemical and physical stability are expected for Apidra® (insulin glulisine, which contains the amino-acid substitutions $Asn^{B3} \rightarrow Lys$ and $Lys^{B29} \rightarrow Glu$).

The decreased chemical stability of the meal-time insulin analogues and their increased susceptibility to fibrillation appears to be intrinsic to their design. Since substitutions were introduced to destabilize the hexamer and therefore make the smaller monomer more available for rapid absorption, a higher proportion of the susceptible monomer will necessarily be present at equilibrium than would be the case with wild-type insulin. It has previously not been clear how this intrinsic problem could be overcome to restore a wild-type level of stability and resistance to fibrillation. Indeed, a series of ten analogues of human insulin, including $Asp^{B28}$-insulin and $Asp^{B10}$-insulin has been tested for susceptibility to fibrillation. All ten were found to be more susceptible to fibrillation at pH 7.4 and 37° C. than is human insulin. The ten substitutions were located at diverse sites in the insulin molecule and are likely to be associated with a wide variation of changes in classical thermodynamic stability. These results suggest that substitutions that protect an insulin analogue from fibrillation under pharmaceutical conditions are rare; no structural criteria or rules are apparent for their design. The present theory of protein fibrillation posits that the mechanism of fibrillation proceeds via a partially folded intermediate state, which in turn aggregates to form an amyloidogenic nucleus. In this theory it is possible that amino-acid substitutions that stabilize the native state may or may not stabilize the partially folded intermediate state and may or may not increase (or decrease) the free-energy barrier between the native state and the intermediate state. It is therefore not obvious from theory whether a given amino-acid substitution in the insulin molecule will increase or decrease the risk of fibrillation in accord with the experimental experience cited above. While it is possible for a particular amino-acid substitution to simultaneously enhance the thermodynamic stability of insulin and its resistance to fibrillation, such substitutions have not been identified. Such concordance would be desirable in a clinical insulin analogue formulation.

Fibrillation, which is a serious concern in the manufacture, storage, and use of insulin and insulin analogues for diabetes treatment, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, diabetic individuals optimally must keep insulin refrigerated prior to use. Fibrillation of insulin or an insulin analogue can be a particular concern for diabetic patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable blood glucose level fluctuations or even dangerous hyperglycemia. At least one recent report has indicated that lispro insulin (an analogue in which residues B28 and B29 are interchanged relative to their positions in wild-type human insulin; trade name Humalog®) may be particularly susceptible to fibrillation and resulting obstruction of insulin pump catheters.

The major barrier to the storage and practical use of presently available pharmaceutical formulations of insulin and insulin analogues at temperatures above 30° C. is accelerated fibrillation of the protein. The major reason for limitations to the shelf life of presently available pharmaceutical formulations of insulin and insulin analogues at temperatures above 10° C. is due to fibrillation of the protein. As noted above, fibrillation is of special concern for fast-acting or "mealtime" insulin analogues (such as Humalog® and Novalog®), particularly when these formulations are diluted by the patient and stored at room temperature for more than 15 days.

Development of fibrillation-resistant insulin analogues would not in itself lead to proteins of indefinite shelf life due to eventual degradation of the protein by chemical modification. Whereas fibrillation represents a change in the structure and spatial relationships between insulin molecules by means of altered non-covalent interactions, chemical modification alters the pattern of covalent bonding between atoms in the insulin molecule. Examples of chemical degradation are breakage of disulfide bridges, formation of non-native disulfide bridges between insulin molecules to form covalent dimers and higher-order polymers, deamination of an asparagine side chain to form an aspartic-acid side chain, and rearrangement of aspartic acid to form iso-aspartic acid within the insulin molecule. Whereas the propensity of an insulin analogue to form fibrils is not correlated with its global thermodynamic stability, enhancing the thermodynamic stability of the insulin molecule has been established to protect the protein from chemical degradation. Therefore, among meal-time analogues, a desirable property would also be enhanced thermodynamic stability to confer simultaneous protection from chemical degradation. The combination of resistance to fibrillation and resistance to chemical degradation would potentially optimize the safe and effective use of an insulin analogue within the reservoir of an insulin pump and to extend the shelf life of an insulin analogue formulation at or above room temperature.

Amino-acid substitutions in insulin have been investigated for effects on thermodynamic stability and biological activity. No consistent relationship has been observed between stability and activity. Whereas some substitutions that enhance thermodynamic stability also enhance binding to the insulin receptor, other substitutions that enhance stability impede such binding. The effects of substitution of $Thr^{A8}$ by several other amino acids has been investigated in wild-type human insulin and in the context of an engineered insulin monomer containing three unrelated substitutions in the B-chain ($His^{B10} \rightarrow Asp$, $Pro^{B28} \rightarrow Lys$, and $Lys^{B29} \rightarrow Pro$) have been reported. Although a range of effects has been observed, no correlation exists between activity and thermodynamic stability. The substitutions $His^{A8}$ and $Arg^{A8}$ have been reported to markedly augment the thermodynamic stability of wild-type human insulin, but the initial studies were conducted at high pH (pH 8.0) and in extremely low ionic strength (10 mM Tris/ClO$_4$—); re-investigation of the $His^{A8}$ analog at pH 7.4 and moderate ionic strength (10 mM potassium phosphate buffer and 50 mM KCl) indicated much smaller effects. The substitution $His^{A8}$ has been reported to delay the fibrillation of wild-type insulin at pH 1.6-2.0 at 60° C. (conditions not relevant to the formulation or use of insulin analogues in the treatment of diabetes mellitus), but its effects at neutral pH and at lower temperatures have not been described. Comparative studies of the kinetics of fibrillation at pH 1.6-2.0 at 60° C. and at pH 7.4 at 37° C. have demonstrated that effects at acidic pH are uncorrelated with effects at neutral pH pertinent to pharmaceutical formulation. No data have been published describing effects of substitutions at A8 or elsewhere on the stability properties of meal-time insulin analogues.

Meal-time insulin analogues are ordinarily formulated as zinc insulin hexamers. Because the process of fibrillation proceeds via a conformationally altered insulin monomer, sequestration of the monomer within a native assembly reduces the concentration of the susceptible monomer. Such assembly also enhances thermodynamic stability, retarding chemical degradation. In addition, insulin assembly damps conformational fluctuations, reducing the rates of both physical and chemical degradation. Because of these advantages, a common method of formulation is to form zinc-stabilized insulin hexamers, the predominant form of the protein in the products Humalin™ (Eli Lilly and Co.), Humalog™ (Eli Lilly and Co.), Novalin™ (Novo-Nordisk), and Novalog™ (Novo-Nordisk). Analogous principles (but in the absence of zinc) pertain to the fast-acting analog Glulisine (Aprida™, manufactured by Sanofi-Aventis). Because of the decreased stability of meal-time insulin analogues, there is a need to identify amino-acid substitutions on the surface of the insulin analogue hexamer that restores or improves the chemical and physical stabilities of the analogue to levels similar to or exceeding those of wild-type human insulin. Such stabilizing substitutions would in principle be beneficial irrespective of whether the insulin analogue is formulated as a solution of soluble zinc-free hexamers, as a solution of soluble zinc hexamers, as a microcrystalline suspension or precipitate of protamine-stabilized zinc hexamers, including but not restricted to regular, NPH, lente, and semi-lente formulations or mixtures thereof.

The problem of chemical degradation and fibrillation is encountered not only among rapid-acting insulin analogues, but also in the formulation of long-acting insulin analogues under acidic conditions. Such analogues, exemplified but not restricted to [$Gly^{A21}$, $Arg^{B31}$, $Arg^{B32}$]-insulin (insulin glargine or Lantus®), contain amino-acid substitutions and/ or extensions of the A- or B-chains designed to shift the isoelectric point of the insulin analogue upward toward neutrality. The analogues are typically formulated as soluble insulin monomers, dimers, and higher-order oligomers at pH<5 under which conditions zinc-mediated assembly is impaired by protonation of $His^{B10}$. Prolonged absorption is achieved by aggregation and precipitation of the insulin analogue in the subcutaneous tissue due to a shift in pH toward 7.4. Under the acidic conditions of formulation, long-acting analogues of this class are susceptible to chemical and physical degradation due to the non-negligible concentration of unprotected monomer in the self-association equilibrium in solution. Therefore, there is a need for amino acid substitutions which stabilize long-acting insulin analogues under conditions of acidic formulation.

SUMMARY OF THE INVENTION

The present invention provides amino-acid substitutions at position A8 of rapid-acting insulin analogues. Without wishing to condition patentability on any particular theory, the A8 side chain is believed to project into solvent from the surface of the A-chain in both an insulin monomer and on its assembly into an insulin hexamer, thus enabling diverse side chains to be accommodated without steric clash.

In the native structure of insulin this position is the C-terminal residue of the A1-A8 α-helix; residues at the end of an α-helix are in general designated C-Cap residues. In wild-type human insulin the residue at position A8 is Thr. In general theories of protein structure and statistical surveys of globular proteins, Thr is considered in principle to be an unfavorable C-Cap residue due to its β-branched side-chain structure. While again not wishing to condition patentability on theory, it is believed that substitutions at A8, as provided herein, enhance its C-Cap propensity (relative to Thr) and hence augment the segmental stability of the A1-A8 α-helix. Irrespective of theory, however, diverse substitutions at A8, when introduced into rapid-acting insulin analogues containing B-chain substitutions known to the art, confer increased thermodynamic stability and increased resistance to fibrillation with maintenance of at least 25% affinity for the insulin receptor relative to wild-type human insulin.

It is, therefore, desired to provide modified meal-time insulin analogues that are more resistant to fibrillation than their original counterparts, while maintaining biological activity and rapid absorption properties.

It is also desired to provide insulin analogues that are more resistant to fibrillation than their counterpart insulin analogues but maintain at least a majority of their biological activity.

It is additionally desired to describe modifications of meal-time insulin analogues that retain high affinity for the insulin receptor without change in cross-binding to the Type I insulin-like growth factor (IGF) receptor.

In general, a method of treating a patient comprises administering a physiologically effective amount of a fibrillation-resistant insulin analogue or a physiologically acceptable salt thereof to the patient, where the fibrillation-resistant insulin analogue or a physiologically acceptable salt thereof contains an insulin A-chain sequence modified at position A8 by substitution with an amino acid with a non-beta-branched side chain. In one example, the substitution is with histidine, lysine, tryptophan or methionine. The fibrillation-resistant insulin or a physiologically acceptable salt thereof possesses a fibrillation lag time greater than a corresponding insulin or insulin analogue that does not possess an insulin A-chain sequence modified at position A8.

A fast-acting vertebrate insulin analogue or a physiologically acceptable salt thereof, contains a substitution at position A8 selected from the group consisting of a histidine substitution, a lysine substitution, a tryptophan substitution, and a methionine substitution and additionally contains at least one other substitution that provides a decreased lag time for activity compared to wild-type insulin, thereby providing a fast-acting insulin analogue. In one example, a substitution that provides for a decreased lag time for activity is an aspartic acid substitution at position B28. In another example, such a substitution is a combination of a lysine substitution at position B28 and a proline substitution at position B29.

An insulin analogue may be an analogue of any vertebrate insulin. In one example, the insulin analogue is a mammalian insulin analogue such as human, murine, bovine, equine, or canine insulin analogues. In other examples, the insulin analogue is an analogue of sheep, whale, rat, elephant, guinea pig or chinchilla insulin.

Specific insulin analogues include those containing SEQ. ID. NOS. 7-10 and 12. A nucleic acid may encode a polypeptide having one of these sequences. Such a nucleic acid may be part of an expression vector, which may be used to transform a host cell.

DETAILED DESCRIPTION OF THE INVENTION

Figure 1A:
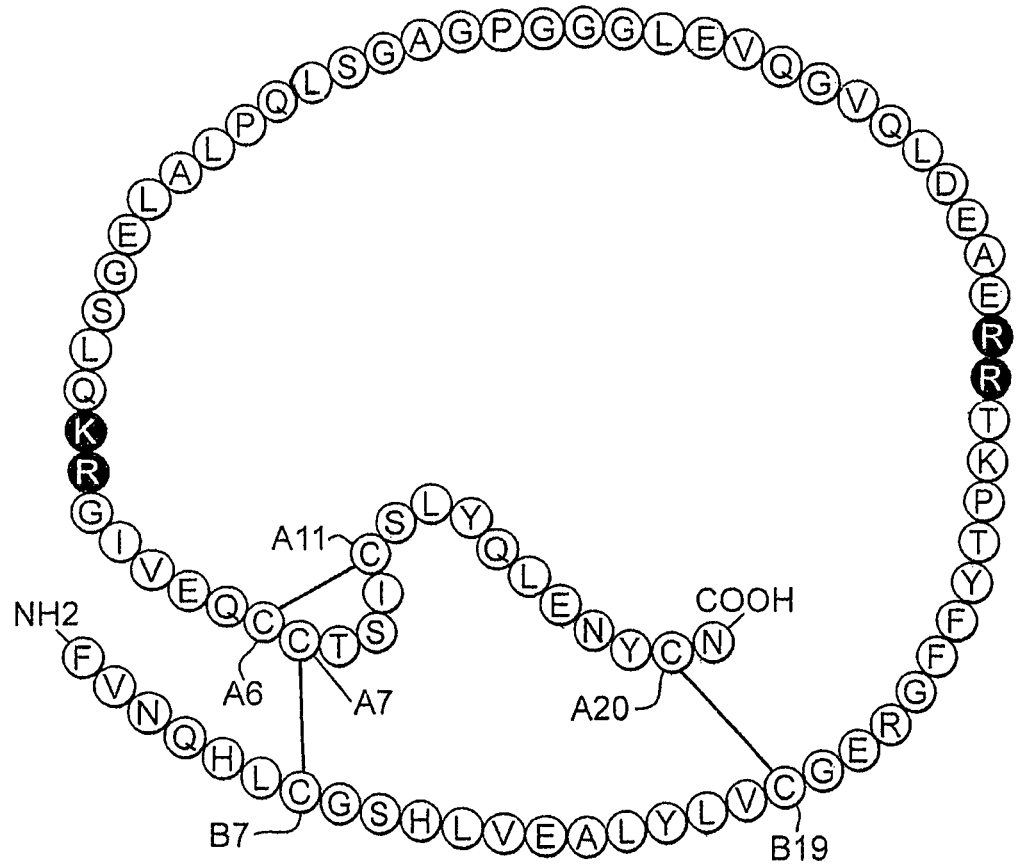
FIG. 1A is a schematic representation of the sequence of human proinsulin including the A- and B-chains and the connecting region shown with flanking dibasic cleavage sites (filled circles) and C-peptide (open circles).
Figure 1B:
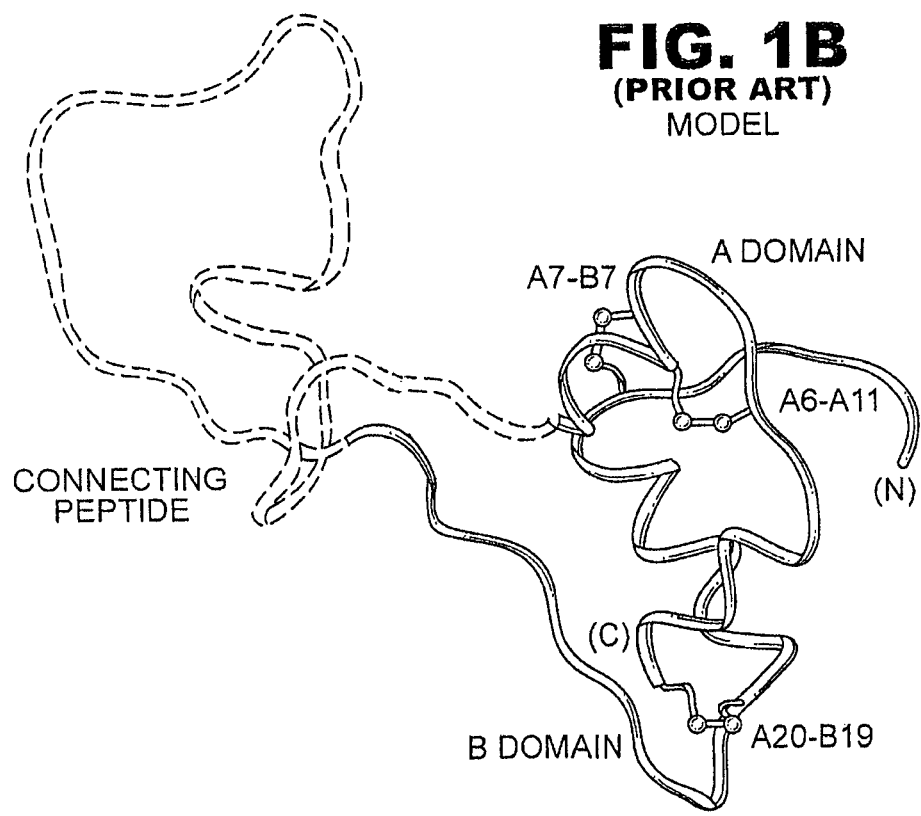
FIG. 1B provides a structural model of proinsulin, consisting of an insulin-like moiety and disordered connecting peptide (dashed line).
Figure 1C:
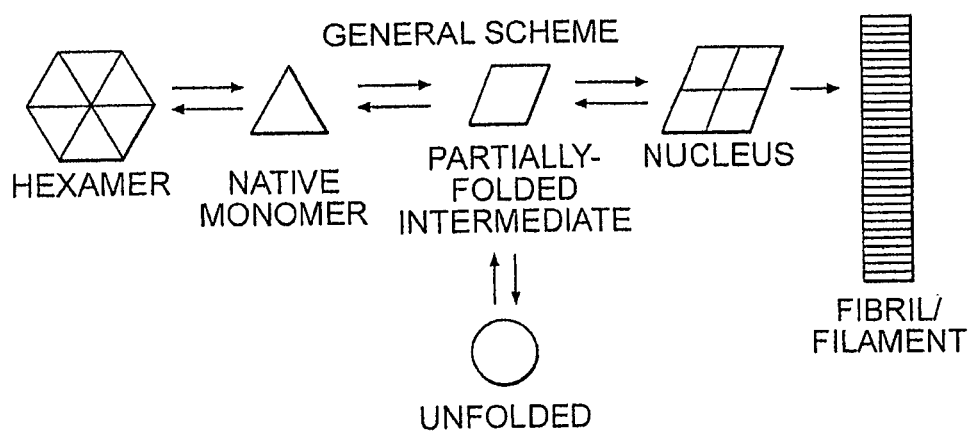
FIG. 1C provides a representation of a proposed pathway of insulin fibrillation via partial unfolding of monomer. The native state is protected by classic self-assembly (far left). Disassembly leads to equilibrium between native- and partially folded monomers (open triangle and trapezoid, respectively). This partial fold may unfold completely as an off-pathway event (open circle) or aggregate to form a nucleus en route to a protofilament (far right).
Figure 1D:
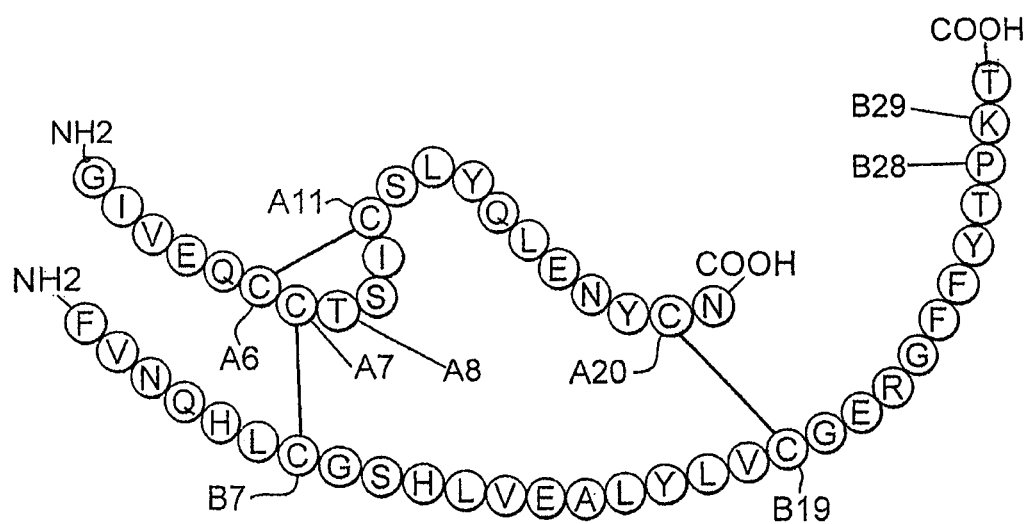
FIG. 1D is a schematic representation of the sequence of human insulin indicating the position of residue A8 in the A-chain and sites of substitution in the B-chain known in the art to confer rapid absorption after subcutaneous injection.
Figure 2:
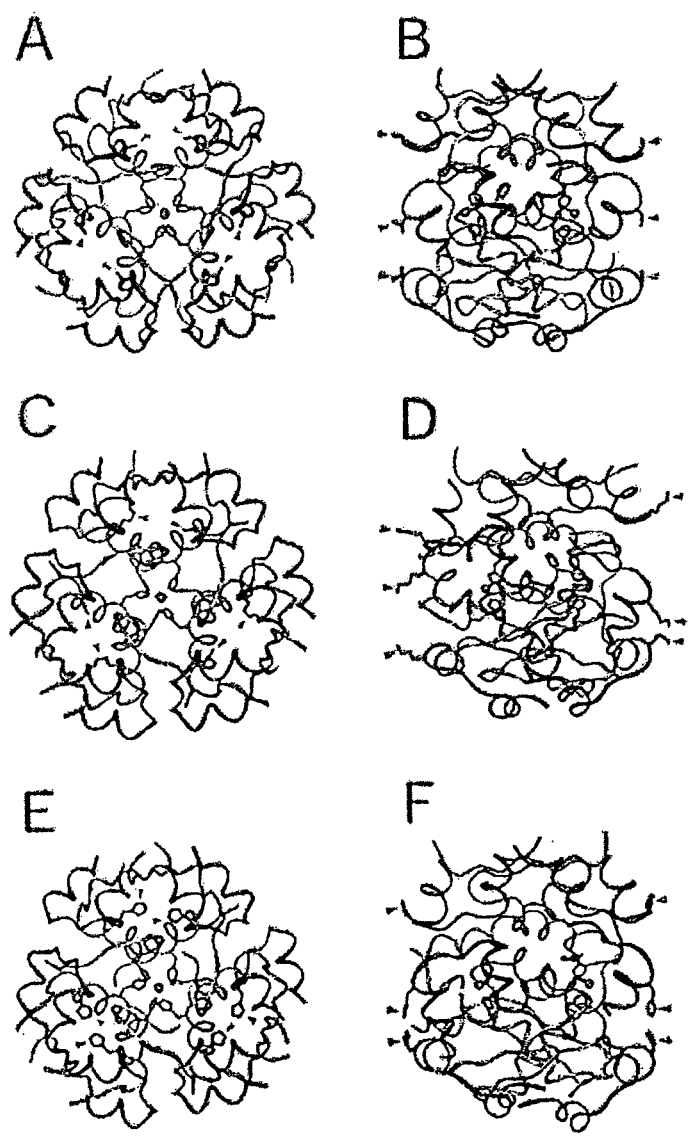
FIG. 2 is a representation of the projected structures of wild-type and variant insulin hexamers as determined by X-ray crystallography as zinc hexamers. T-state protomers are shown in panels A-C; R-state protomers are shown in panels D-F. The T-state is thought to best represents the structure of an insulin monomer whereas insulin and insulin analogues within pharmaceutical formulations are often stabilized as R-state conformations. (A and D) wild-type human insulin; (B and E) $Lys^{A8}$-insulin, (C and F) $His^{A8}$-insulin. The polypeptide main chains are shown as ribbons. In each panel the A-chain is shown in black, B-chain in gray, and zinc ions are represented by spheres. The locations of the A8 side chains are indicated with arrowheads.
Figure 3:
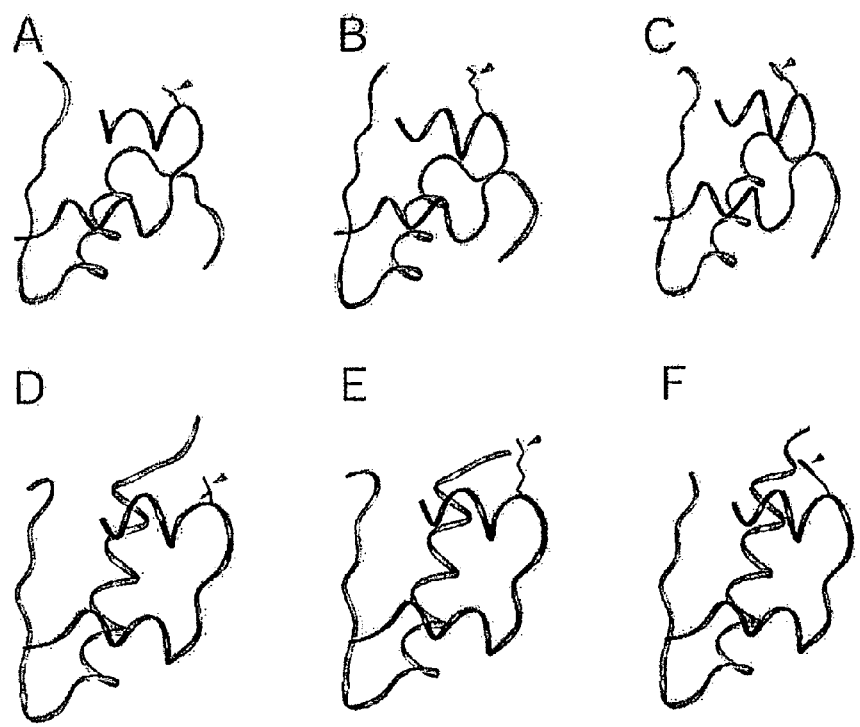
FIG. 3 is a representation of projected structures of T-state protomers and R-state protomers as determined by X-ray crystallography. T-state protomers are shown in the upper row (panels A-C); $R^f$ state protomers are shown in the lower row (D-F). (A and D) wild-type human insulin; (B and E) $Lys^{A8}$-insulin, and (C and F) $His^{A8}$-insulin. The locations of the A8 side chains are indicated with arrowheads.

The present invention is directed toward augmenting the thermodynamic stability of rapid-acting insulin analogues and their resistance to fibrillation to facilitate their use in treatment of diabetes, particularly their use in insulin delivery via implantable or external pumps. To that end, the present invention provides insulin analogues that contain an amino-acid substitution at position A8 of the A-chain polypeptide and an insulin B-chain polypeptide containing one or more substitutions, either currently unknown or known in the art, to confer rapid absorption following subcutaneous injection. Another aspect of the present invention is the use of amino-acid substitutions at position A8 to augment the stability of other classes of insulin analogues and to enhance their resistance to fibrillation.

The insulin analogues of the present invention may also contain other modifications. As used in this specification and the claims, various substitution analogues of insulin may be noted by the convention that indicates the amino acid being substituted, followed by the position of the amino acid, optionally in superscript. The position of the amino acid in question includes the A- or B-chain of insulin where the substitution is located. For example, an insulin analogue of the present invention may also contain a substitution of Aspartic acid (Asp or D) or Lysine (Lys or K) for Proline (Pro or P) at amino acid 28 of the B-chain (B28), or a substitution of Pro for Lys at amino acid 29 of the B-chain (B29) or a combination thereof. These substitutions may also be denoted as Asp$^{B28}$, Lys$^{B28}$, and Pro$^{B29}$, respectively. Unless noted otherwise or wherever obvious from the context, the amino acids noted herein should be considered to be L-amino acids.

The Asp$^{B28}$ substitution is present in the insulin analogue known as Aspart insulin and sold as Novalog® whereas the Lys$^{B28}$ and Pro$^{B29}$ substitutions are present in the insulin analogue known as Lispro insulin and sold under the name Humalog®. These analogues are described in U.S. Pat. Nos. 5,149,777 and 5,474,978, the disclosures of which are hereby incorporated by reference herein. Both of these analogues are known as fast-acting insulins, but are also known to have increased propensity to aggregate and form fibrils.

The invention provides insulin analogues that are more resistant to fibrillation than their counterpart insulin analogues but maintain at least a majority of their biological activity. Examples are provided by introducing substitutions at the A8 position of Asp$^{B28}$-insulin (the meal-time insulin analogue formulated in Novalog®) and at the A8 position of [Lys$^{B28}$, Pro$^{B29}$]-insulin (the meal-time insulin analogue formulated in Humalog®). In one example, a modification of Humalog by the substitution His$^{A8}$ is shown to restore its thermodynamic stability and resistance to fibrillation to levels similar to wild-type human insulin. In another example, a modification of Humalog by the substitution Lys$^{A8}$ is shown likewise to restore its thermodynamic stability and resistance to fibrillation to levels similar to wild-type human insulin. The diverse side chains of these amino acids are well accommodated at the surface of the zinc insulin hexamer. These results are extended to related examples in which the same substitutions (His$^{A8}$ or Lys$^{A8}$) are introduced into Asp$^{B28}$-insulin as a modification of the meal-time insulin analogue formulated in Novalog®. In still another example, a modification of Humalog by the substitution Trp$^{A8}$ is shown to improve its thermodynamic stability and resistance to fibrillation.

It is envisioned that other amino-acid substitutions at position A8 may also confer improved thermodynamic stability and resistance to fibrillation of an insulin analogue while maintaining at least a majority of the activity of the analogue. These include but are not restricted to other amino acids having an amine-containing side chain, that is, glutamine, asparagine, lysine, arginine, or histidine.

A method for treating a patient comprises administering a fibrillation-resistant insulin analogue to the patient. In one example, the fibrillation-resistant insulin analogue is an insulin analogue containing both (a) substitutions at internal interfaces of the insulin hexamer designed to confer rapid absorption after subcutaneous or intraperitoneal absorption and (b) one or more substitutions elsewhere in the insulin molecule designed to restore chemical stability and physical stability to levels similar to wild-type human insulin. In another example, the insulin analogue is administered by an external or implantable insulin pump.

It is also envisioned that it would be possible to apply the introduction of substitutions at position A8 to other classes of insulin analogues (such as long-acting analogs formulated at acidic pH and designed to exhibit a higher isoelectric point than wild-type human insulin) for one or all of the purposes of augment thermodynamic stability, decreasing rates of chemical degradation, and increasing resistance to fibrillation.

It is further envisioned that it would be possible to apply the introduction of substitutions at position A8 in other classes of formulations of insulin analogues (such as but not restricted to regular, NPH, semi-lente and lente, including mixtures of such types) for one or more of the purposes of augment thermodynamic stability, decreasing rates of chemical degradation, and increasing resistance to fibrillation.

It has been discovered that substitutions at position A8 can prevent a significant increase in cross-binding by an insulin analogue to the Type I IGF receptor and to prevent a significant increase in mitogenicity.

In general, a vertebrate insulin analogue or a physiologically acceptable salt thereof, comprises a insulin analogue containing an insulin A-chain and an insulin B-chain. An insulin analogue of the present invention may also contain other modifications, such as substitutions of a histidine at residues A4, A8 and B1 as described more fully in co-pending U.S. application Ser. No. 12/160,187, the disclosure of which is incorporated by reference herein. In one example, the vertebrate insulin analogue is a mammalian insulin analogue, such as a human, porcine, bovine, feline, canine or equine insulin analogue. An insulin analogue of the present invention may also contain other modifications, such as a tether between the C-terminus of the B-chain and the N-terminus of the A-chain as described more fully in co-pending U.S. application Ser. No. 12/419,169, the disclosure of which is incorporated by reference herein.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. In another example, a pharmaceutical composition including a single-chain insulin analogue displays less than 1 percent fibrillation at 37° C. at a zinc molar ratio of less than 2, 1.5, 1 per hexamer or even in the absence of zinc other than that amount present as an impurity. Modifications of meal-time insulin analogues may be formulated as described for (a) "regular" formulations of Humulin™ (Eli Lilly and Co.), Humalog™ (Eli Lilly and Co.), Novalin™ (Novo-Nordisk), and Novalog™ (Novo-Nordisk) and other rapid-acting insulin formulations currently approved for human use, (b) "NPH" formulations of the above and other insulin analogues, and (c) mixtures of such formulations.

Excipients may include glycerol, glycine, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding an A-chain with a substitution of histidine, lysine or tryptophan at position A8 is also envisioned. The particular sequence may depend on the preferred codon usage of a species in which the nucleic acid sequence will be introduced. The nucleic acid may also encode other modifications of wild-type insulin. The nucleic acid sequence may encode a modified A- or B-chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an *E. coli* cell line, or a eukaryotic cell line such as *S. cerevisiae* or *Pischia pastoris* strain or cell line.

Chemical degradation of insulin, such as deamination, isopeptide bond formation, and disulfide interchange leading to formation of covalent polymers, is known to be reduced by formulations or modifications that enhance the thermodynamic stability of the native molecular structure of the insulin or insulin analogue. The present invention describes amino-acid substitutions in the A-chain of an insulin analogue that counter-acts the destabilizing effects of amino-acid substitutions previously described in the B-chain and in current use as rapid-acting insulin formulations.

As mentioned above, the diversity of amino-acid side chains tolerated at position A8 with respect to the structure of the insulin monomer and hexamer and with respect to maintenance of at least 25% of the receptor-binding activity of wild-type human insulin makes possible the incorporation of A8 residues of positive charge, negative charge, or without charge as a means to modulate the isoelectric point of an insulin analogue. Adjusting the isoelectric point of an insulin analogue can be of pharmacological interest as a means to enhance or impair solubility at pH 7.4 and as a means to reduce the risk of unfavorable isoelectric precipitation of the protein during storage and use in an insulin pump.

Substitutions with amino acids other than those containing nitrogenous side chains are also envisioned. For example, substitution of threonine by glutamate at A8 stabilizes insulin analogues. Although $Glu^{A8}$ also reduces activity about 2-3 fold compared to $Thr^{A8}$ insulin and insulin analogues, this level of activity may be acceptable for some applications. Additional A8 substitutions that are envisioned include arginine, phenylalanine, tyrosine and other non-beta-branched amino acid substitutions.

It is further envisioned that A8 substitutions can be designed to reduce cross-binding of insulin analogues to the IGF Type I receptor and hence the mitogenicity and potential carcinogenicity of the analogue.

Still other substitutions are also compatible with the insulin analogues of the present invention. In addition to the fast-acting class of insulin analogues, A8 substitutions may be employed to enhance the thermodynamic stability of long-acting insulin analogs and their resistance to chemical degradation and fibrillation. An example is provided by (but not restricted to) insulin glargine (Lantus®), which is formulated at pH 4 under which conditions zinc-mediated assembly does not occur.

It is also envisioned that the intrinsic resistance of A8-modified insulin analogues to fibrillation makes it unnecessary to formulate such analogues as zinc-stabilized hexamers or other higher-order oligomers. Because disassembly of the zinc-stabilized hexamer ordinarily delays absorption of insulin or insulin analogues in current formulations, it is envisioned that a fibrillation-resistant formulation of an A8-stabilized insulin analogue as a zinc-free insulin monomer or dimer would confer more rapid adsorption into the blood stream following subcutaneous injection.

It is further envisioned that the insulin analogues of the present invention may also utilize any of a number of changes present in existing insulin analogues, modified insulins, or within various pharmaceutical formulations, such as regular insulin, NPH insulin, lente insulin or ultralente insulin, in addition to human insulin. The insulin analogues of the present invention may also contain substitutions present in analogues of human insulin that, while not clinically used, are still useful experimentally, such as DKP-insulin, which contains the substitutions $Asp^{B10}$, $Lys^{B28}$ and $Pro^{B29}$ or the $Asp^{B9}$ substitution. The present invention is not, however, limited to human insulin and its analogues. It is also envisioned that these substitutions may also be made in animal insulins such as porcine, bovine, equine, and canine insulins, by way of non-limiting examples. Furthermore, in view of the similarity between human and animal insulins, and use in the past of animal insulins in human diabetic patients, it is also envisioned that other minor modifications in the sequence of insulin may be introduced, especially those substitutions considered "conservative" substitutions. For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E).

The amino acid sequence of human proinsulin is provided, for comparative purposes, as SEQ. ID. NO. 1. The amino acid sequence of the A-chain of human insulin is provided as SEQ. ID. NO. 2. The amino acid sequence of the B-chain of human insulin is provided, for comparative purposes, as SEQ. ID. NO. 3.

SEQ. ID. NO. 1
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr-Arg-Arg-Glu-Ala-Glu-Asp-

Leu-Gln-Val-Gly-Gln-Val-Glu-Leu-Gly-Gly-Gly-Pro-

Gly-Ala-Gly-Ser-Leu-Gln-Pro-Leu-Ala-Leu-Glu-Gly-

Ser-Leu-Gln-Lys-Arg-Gly-Ile-Val-Glu-Gln-Cys-Cys-

Thr-Ser-Ile-Cys-Ser-Leu-Tyr-Gln-Leu-Glu-Asn-Tyr-

Cys-Asn

SEQ. ID. NO. 2
Gly-Ile-Val-Glu-Gln-Cys-Cys-Thr-Ser-Ile-Cys-Ser-

Leu-Tyr-Gln-Leu-Glu-Asn-Tyr-Cys-Asn

SEQ. ID. NO. 3
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

Various substitutions, including substitutions of prior known insulin analogues, may also be present in the insulin analogue of the present invention. For example, an amino acid sequence of an insulin analogue B-chain also carrying the $Lys^{B28}$ $Pro^{B29}$ substitutions of lispro insulin is provided as SEQ. ID. NO 4 Likewise, an amino acid sequence of an insulin analogue B-chain carrying the $Asp^{B28}$ substitution of aspart insulin is provided as SEQ. ID. NO. 5. Additionally, exemplary amino acid sequences of an insulin analogue B-chain also carrying the $Asp^{B10}$ substitution are provided as SEQ. ID. NO. 6.

SEQ. ID. NO. 4
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Lys-Pro-Thr

SEQ. ID. NO. 5
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Asp-Thr

SEQ. ID. NO. 6
Phe-Val-Asn-Gln-His-Leu-Cys-Gly-Ser-Asp-Leu-Val-

Glu-Ala-Leu-Tyr-Leu-Val-Cys-Gly-Glu-Arg-Gly-Phe-

Phe-Tyr-Thr-Pro-Lys-Thr

It is envisioned that the increased activity of the $His^{A8}$, $Lys^{A8}$, and $Trp^{A8}$ substitutions will provide an insulin analogue that has increased activity compared to natural insulin but does not have an affinity for Type I Insulin-like Growth Factor Receptor (IGFR) that is more than twofold higher than that of normal insulin. Insulin or insulin analogue activity may be determined by receptor binding assays as described in more detail herein below. Relative activity may be defined in terms of $ED_{50}$ values, the concentration of unlabelled insulin or insulin analogue required to displace 50 percent of specifically bound labeled human insulin such as a radioactively-labeled human insulin (such as $^{125}$I-labeled insulin) or radioactively-labeled high-affinity insulin analog. Alternatively, activity may be expressed simply as a percentage of normal insulin. Affinity for the insulin-like growth factor receptor may also be determined in the same way with displacement from IGFR being measured. In particular, it is desirable for an insulin analogue to have an activity that is greater than 100 percent of insulin, such as 110, 120, 130, 140, 150, or 200 percent of normal insulin or more, while having an affinity for IGFR that is less than or equal to 100 percent of normal insulin, such as 90, 80, 70, 60 or 50 percent of normal insulin or less. It is desirable to determine insulin activity in vitro as described herein, rather than in vivo. It has been noted that in vivo, clearance of insulin from the bloodstream is dependent on receptor binding. In this way, insulin analogues may exhibit high activity, even approaching approximately 100 percent activity in vivo, even though they are less active at the cellular level, due to slower clearance from the bloodstream. However, an insulin analogue can still be useful in the treatment of diabetes even if the in vitro receptor-binding activity is as low as 20% due to this slower clearance.

A-chain analogues of insulin containing amino-acid substitutions at position A8 were made by total chemical synthesis of the variant A-chain. Wild-type- and variant B-chains were obtained from commercial formulations of human insulin or insulin analogues by oxidative sulfitolysis. The insulin analogue was obtained by insulin chain combination followed by chromatographic purification. In each case the predicted molecular mass was verified by mass spectrometry.

Insulin analogues were synthesized containing the A8 substitutions (His or Lys) shown generally as SEQ. ID. NO. 7. For comparative purposes, analogues were synthesized in the context of a wild-type B-chain, $Asp^{B28}$ B-chain or [$Lys^{B28}$, $Pro^{B29}$] B-chain. Comparison of the properties of these analogues with human insulin, $Asp^{B28}$-insulin, and/or [$Lys^{B28}$, $Pro^{B29}$]-insulin indicates the general effects of the diverse A8 substitutions to simultaneously enhance activity, thermodynamic stability, and resistance to fibrillation. In no case did the A8 substitutions increase cross-binding to the IGFR by more than twofold.

SEQ. ID. NO. 7
Gly-Ile-Val-Glu-Gln-Cys-Cys-Xaa$_1$-Ser-Ile-Cys-Ser-

Leu-Tyr-Gln-Leu-Glu-Asn-Tyr-Cys-Asn
Xaa$_1$ = His, Lys, Arg, Phe, Tyr

Insulin analogues having the A-chain polypeptide sequences of SEQ. ID. NOS. 8-10 were prepared. These analogues contain A8 substitutions, in concert with B-chain substitutions [$Lys^{B28}$, $Pro^{B29}$] (SEQ. ID. NO 4) to permit their comparison to the fast-acting analogue in Humalog (i.e., in which Pro at position B28 is replaced by Lys, and Lys at position B29 is replaced by Pro). The analogue was synthesized and tested for activity and resistance to fibrillation. Fibrillation was assayed under zinc-free conditions to focus on the intrinsic properties of the susceptible monomer. The physical and chemical stabilities of the analogue were evaluated in triplicate during incubation in 60 µM phosphate-buffered saline (PBS) at pH 7.4 at 37° C. under gentle agitation. The samples were observed for 10 days or until signs of precipitation or frosting of the glass vial were observed. The time course of fibrillation was monitored at serial time points by Thioflavin (ThT) fluorescence. Whereas [Lys$^{B28}$, Pro$^{B29}$]-insulin forms fibrils two- to threefold more quickly than does wild-type human insulin, incorporation of the His$^{A8}$ or Lys$^{A8}$ substitution restores its resistance to fibrillation to the level exhibited by wild-type human insulin. The resistance of Trp$^{A8}$-[Lys$^{B28}$, Pro$^{B29}$]-insulin to fibrillation was intermediate between [Lys$^{B28}$, Pro$^{B29}$]-insulin and human insulin. Whereas [Lys$^{B28}$, Pro$^{B29}$]-insulin exhibits reduced thermodynamic stability relative to human insulin (as inferred from chemical denaturation experiments; below), incorporation of the His$^{A8}$, Lys$^{A8}$ or Trp$^{A8}$ substitutions restores its stability to levels similar to or greater than that of wild-type human insulin. The A8 substitutions in each case augmented the affinity of the insulin analogue for the insulin receptor.

SEQ. ID. NO. 8
Gly-Ile-Val-Glu-Gln-Cys-Cys-His-Ser-Ile-Cys-Ser-

Leu-Tyr-Gln-Leu-Glu-Asn-Tyr-Cys-Asn

SEQ. ID. NO. 9
Gly-Ile-Val-Glu-Gln-Cys-Cys-Lys-Ser-Ile-Cys-Ser-

Leu-Tyr-Gln-Leu-Glu-Asn-Tyr-Cys-Asn

SEQ. ID. NO. 10
Gly-Ile-Val-Glu-Gln-Cys-Cys-Trp-Ser-Ile-Cys-Ser-

Leu-Tyr-Gln-Leu-Glu-Asn-Tyr-Cys-Asn

Insulin analogues having the polypeptide sequences of SEQ. ID. NOS. 8-10 for the insulin A-chain were likewise prepared with a polypeptide sequence of SEQ. ID. NO 5 for the insulin B-chain. These analogues contain A8 substitutions in concert with B-chain substitutions Asp$^{B28}$ to permit their comparison to the fast-acting insulin analogue in Novalog (i.e., in which Pro at position B28 is replaced by Asp). A similar pattern of protective effects was observed relative to Asp$^{B28}$-insulin as described above in the context of [Lys$^{B28}$, Pro$^{B29}$]-insulin. The A8 substitutions likewise augmented the affinity of the insulin analogue for the insulin receptor.

Receptor-Binding Assays—Relative activity is defined as the ratio of analogue to wild-type human insulin required to displace 50 percent of specifically bound $^{125}$I-human insulin. Data was corrected for nonspecific binding (amount of radioactivity remaining membrane associated in the presence of 1 µM human insulin). In all assays, the percentage of tracer bound in the absence of competing ligand was less than 15% to avoid ligand-depletion artifacts. Relative affinities of insulin analogues for the isolated insulin holoreceptor (isoform A) were performed using a microtiter plate antibody capture technique as known in the art. Microtiter strip plates (Nunc Maxisorb) were incubated overnight at 4° C. with AU5 IgG (100 µl/well of 40 mg/ml in phosphate-buffered saline). Binding data were analyzed by a two-site sequential model. A corresponding microtiter plate antibody assay using the IGF Type I receptor was employed to assess cross-binding to this homologous receptor.

The relative affinities for various insulin analogues are provided in Table 1 below. The receptor-binding affinity of wild-type human insulin for the human insulin receptor (isoform A) under these conditions is 0.034±0.002 nM. Error estimates are in each case less than ±10%. KP=Humalog (lispro); Asp$^{B28}$ human insulin=Novalog.

TABLE 1

Affinity for Insulin Receptor (relative to human insulin)

| Sample: | Affinity for Insulin Receptor: |
|---|---|
| Human insulin (SEQ. ID. NOS. 2 & 3) | 100% |
| KP-insulin (SEQ. ID. NOS. 2 & 4) | 110% |
| His$^{A8}$-human-insulin (SEQ. ID. NOS. 3 & 8) | 212% |
| His$^{A8}$-KP-insulin (SEQ. ID. NOS. 4 & 8) | 162% |
| Lys$^{A8}$-human-insulin (SEQ. ID. NOS. 3 & 9) | 126% |
| Lys$^{A8}$-KP-insulin (SEQ. ID. NOS. 4 & 9) | 310% |
| Trp$^{A8}$-KP-insulin (SEQ. ID. NOS. 4 & 10) | 212% |
| Asp$^{B28}$-human-insulin (SEQ. ID. NOS. 2 & 5) | 147% |
| His$^{A8}$-Asp$^{B28}$-insulin (SEQ. ID. NOS. 5 & 8) | 189% |

These data indicate that the affinity of the analogues to the human insulin receptor is as great or greater than that of wild-type human insulin.

The affinities of these insulin analogues for the IGF Type I receptor is similar to that of human insulin; the extent of increased affinity, if present, is less than two-fold that of human insulin. The relative affinities of insulin analogues were determined as shown in Table 2. The receptor-binding affinity of wild-type human insulin for the Type I IGF under these conditions receptor is 9.57±0.31 nM. Error estimates are in each case less than ±10%.

TABLE 2

Relative Affinities of Insulin Analogs For the Human IGF Receptor

| Sample | Affinity for IGFR (compared to that of human insulin) |
|---|---|
| Human insulin (SEQ. ID. NOS. 2 & 3) | 100 |
| KP-insulin (SEQ. ID. NOS. 2 & 4) | 90 |
| His$^{A8}$-human-insulin (SEQ. ID. NOS. 3 & 8) | 148 |
| His$^{A8}$-KP-insulin (SEQ. ID. NOS. 4 & 8) | 133 |
| Lys$^{A8}$-human-insulin (SEQ. ID. NOS. 3 & 9) | 65 |
| Lys$^{A8}$-KP-insulin (SEQ. ID. NOS. 4 & 9) | 108 |
| Trp$^{A8}$-KP-insulin (SEQ. ID. NOS. 4 & 10) | 174 |
| Asp$^{B28}$-human-insulin (SEQ. ID. NOS. 2 & 5) | 185 |
| His$^{A8}$-Asp$^{B28}$-insulin (SEQ. ID. NOS. 5 & 8) | 121 |

As the data above indicate, His, Lys, and Trp substitutions at A8 maintain the insulin activity of analogues containing such substitutions while keeping cross-reactivity with Type I Insulin-Like Growth Factor (IGF) Receptor below a level twice that of wild-type insulin.

The thermodynamic stabilities of the insulin analogues were evaluated by guanidine denaturation (Table 3). Data were obtained at 37° C. and neutral pH to correspond to the conditions of insulin use.

TABLE 3

Thermodynamic Stabilities of Insulin Analogues (37° C. and pH 7.4)

| Sample | Stability ($\Delta G_u$) |
|---|---|
| Human insulin (SEQ. ID. NOS. 2 & 3) | 3.3 ± 0.1 |
| KP-insulin (SEQ. ID. NOS. 2 & 4) | 2.8 ± 0.1 |
| His$^{A8}$-human-insulin (SEQ. ID. NOS. 3 & 8) | 3.9 ± 0.1 |
| His$^{A8}$-KP-insulin (SEQ. ID. NOS. 4 & 8) | 3.9 ± 0.1 |
| Lys$^{A8}$-human-insulin (SEQ. ID. NOS. 3 & 9) | 3.7 ± 0.1 |
| Lys$^{A8}$-KP-insulin (SEQ. ID. NOS. 4 & 9) | 3.2 ± 0.1 |
| Trp$^{A8}$-KP-insulin (SEQ. ID. NOS. 4 & 10) | 3.7 ± 0.1 |
| Asp$^{B28}$-human-insulin (SEQ. ID. NOS. 2 & 5) | 2.9 ± 0.1 |
| His$^{A8}$-Asp$^{B28}$-insulin (SEQ. ID. NOS. 5 & 8) | 3.7 ± 0.1 |

As shown in Table 3, His[48], Lys[48] and Trp[48] substitutions do not significantly lower, and actually increase the stability of the resulting insulin analogue.

The effect of the A8 substitutions on secondary structure were also examined as follows.

Figure 4A:
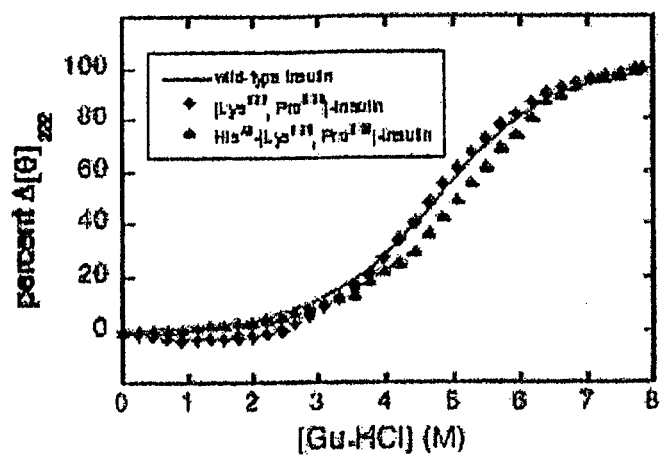
FIG. 4A is a graph of CD-monitored guanidine denaturation of His$^{A8}$-[Lys$^{B28}$, Pro$^{B29}$]-insulin analog (▲) relative to [Lys$^{B28}$, Pro$^{B29}$]-insulin (♦, Humalog®) and wild-type human insulin (solid line).
Figure 4B:
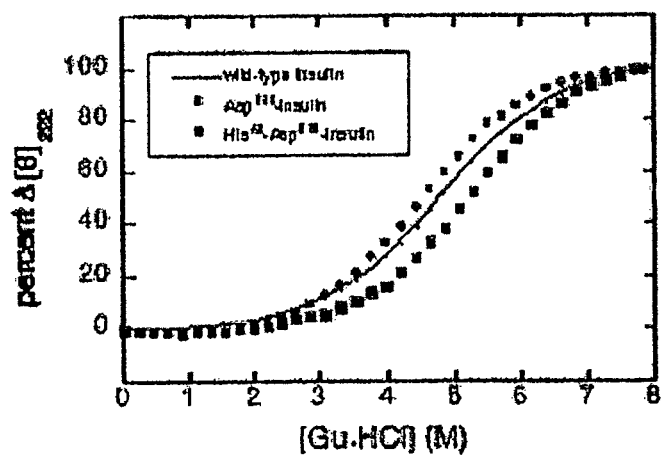
FIG. 4B is a graph of CD-monitored guanidine denaturation of His$^{A8}$-[Asp$^{B28}$]-insulin (■) relative to [Asp$^{B28}$]-insulin (●, Novalog®) and wild-type human insulin (solid line).

Circular Dichroism—Samples were dissolved in either 10 mM phosphate and 100 mM KCl (pH 7.4) at a protein concentration of 25 μM. To remove particulate matter and protein aggregates, samples were filtered (0.22 μM; Satorius, Goetlingen, Germany). Spectra, acquired with an Aviv spectropolarimeter (Aviv Biomedical, Inc., Lakewood, N.J.), were normalized. Data were obtained at 25° C. and fitted by non-linear least squares to a two-state model. CD Spectra for His[48]-containing analogues were similar to their wild type and fast-acting analogue counterparts as shown in FIGS. 4A and 4B. FIG. 4A shows the CD-monitored guanidine denaturation of His[48]-[Lys$^{B28}$, Pro$^{B29}$,]-insulin analog (▲), relative to [Lys$^{B28}$, Pro$^{B29}$]-insulin (♦, Humalog®) and wild-type human insulin (solid line). FIG. 4B shows the CD monitored guanidine denaturation of His[48]-[Asp$^{B28}$]-insulin (■) relative to [Asp$^{B28}$]-insulin (●, Novalog®) and wild-type human insulin (solid line).

The effect of the A8 substitutions on fibrillation time were also examined as follows.

Fibrillation Assay—Human insulin and analogues were made 60 μM in a deoxygenated buffer consisting of 10 mM sodium phosphate (pH 7.4), and 140 mM NaCl. Samples (in triplicate) were placed in sealed glass vials and placed on an automated tilting table at 37° C. At successive times aliquots were withdrawn and analyzed by a thioflavin T (ThT) fluorescence spectroscopy assay to determine the onset of fibrillation as follows.

Thioflavin T (ThT) was made 1 mM in double-distilled water and stored at 4° C. in the dark. To monitor fibrillation, 10-μl aliquots of samples were obtained at indicated time points and were mixed with 3 ml of ThT assay buffer (5 μM ThT in 50 mM Tris-HCl (pH 7.5) and 100 mM NaCl). Fluorescence measurements were performed using an Aviv spectrofluorometer in 1-cm quartz cuvettes. Emission spectra were collected from 470 to 500 nm following excitation at 450 nm; the integration time was 1 s. ThT in buffer without protein was used as baseline. The fibrillation lag time is defined as the time required to observe twofold enhancement in ThT emission. The threshold of twofold-enhanced ThT fluorescence is followed a rapid increase in turbidity associated with elongation of mature fibrils and a further increase in ThT fluorescence. Under these conditions, human insulin undergoes fibrillation in 3-4 days in the absence of zinc. Lag times prior to fibrillation of the analogues at a protein concentration of 60 μM are provided in Table 4.

Transmission Electron Microscopy—The presence or absence of fibrils (as distinct from amorphous precipitation or crystals) was verified by TEM. Aliquots (10 μl) were deposited on Formvar-coated 400-mesh copper grids (Electron Microscopy Sciences, Hatfield, Pa.) for 5 min. Excess solution was adsorbed to filter paper. Grids were washed three times with distilled water and three times with filtered 1% uranyl acetate for negative staining. Stained grids were allowed to dry for 20 min at room temperature. Specimens were observed with a Jeol 1200EX transmission electron microscope operating with an accelerating voltage of 80 kV.

TABLE 4

Fibrillation Lag Times of zinc free-insulin and analogues at 60 μM

| Sample | Lag time (days) |
|---|---|
| Human insulin (SEQ. ID. NOS. 2 & 3) | 3.5 ± 0.6 |
| KP-insulin (SEQ. ID. NOS. 2 & 4) | 2.6 ± 0.3 |
| His[48]-human-insulin (SEQ. ID. NOS. 3 & 8) | 13 ± 2.6 |
| His[48]-KP-insulin (SEQ. ID. NOS. 4 & 8) | 6.2 ± 0.8 |
| Lys[48]-human-insulin (SEQ. ID. NOS. 3 & 9) | ND |
| Lys[48]-KP-insulin (SEQ. ID. NOS. 4 & 9) | 6.3 ± 0.6 |
| Trp[48]-KP-insulin (SEQ. ID. NOS. 4 & 10) | 4.2 ± 0.3 |
| Asp$^{B28}$-human-insulin (SEQ. ID. NOS. 2 & 5) | 1.7 ± 0.3 |
| His[48]-Asp$^{B28}$-insulin (SEQ. ID. NOS. 5 & 8) | 5.8 ± 0.3 |

ND = Not Determined

Figure 5A:
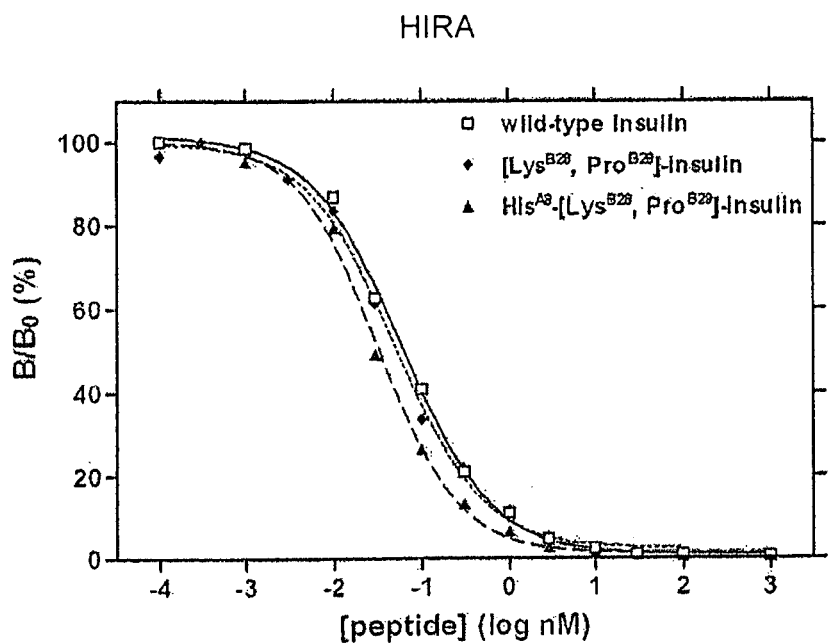
FIG. 5A is a graph of the results of a receptor-binding assay showing the specific binding of His$^{A8}$-[Lys$^{B28}$, Pro$^{B29}$]-insulin analog (▲), [Lys$^{B28}$, Pro$^{B29}$]-insulin (♦, Humalog®) and wild-type human insulin (solid line) to the human insulin receptor over a range of peptide concentrations.
Figure 5B:
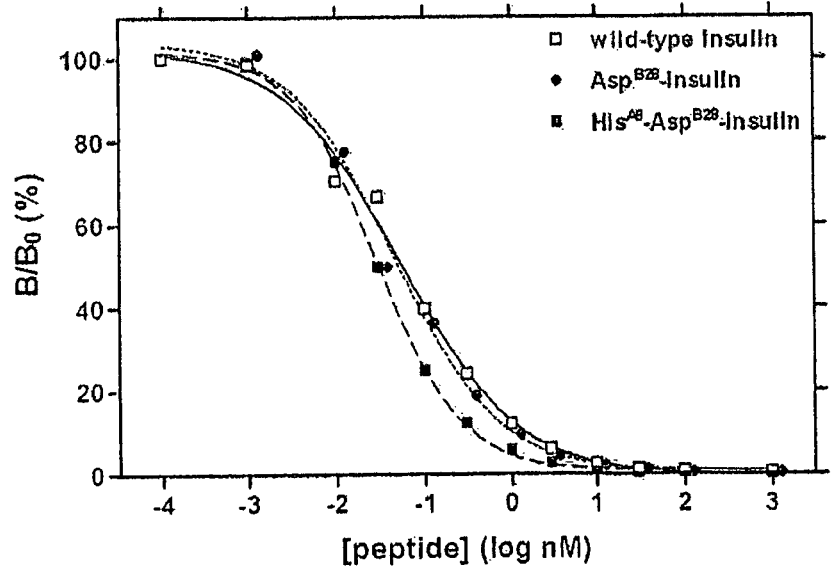
FIG. 5B is a graph of the results of a receptor-binding assay showing the specific binding of His$^{A8}$-[Asp$^{B28}$]-insulin (■) relative to [Asp$^{B28}$] (●, Novalog®) and wild-type human insulin (solid line) to the human insulin receptor over a range of peptide concentrations.
Figure 5C:
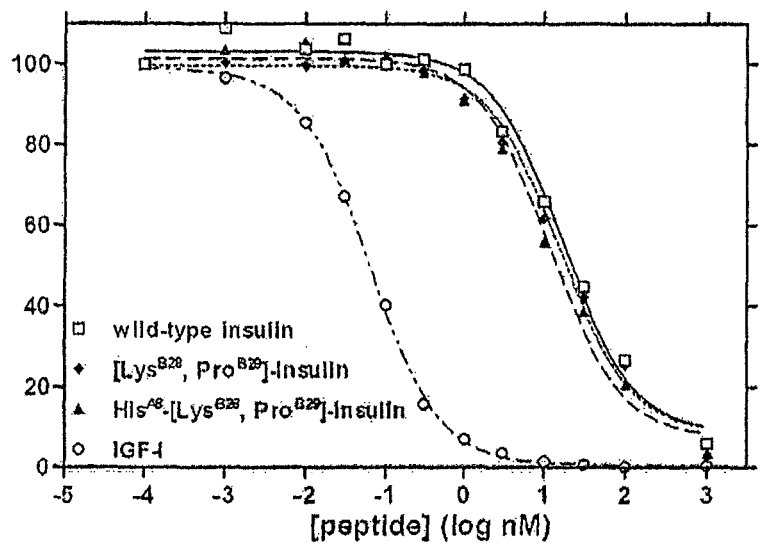
FIG. 5C is a graph of the results of a receptor-binding assay showing the specific binding of His$^{A8}$-[Lys$^{B28}$, Pro$^{B29}$]-insulin analog (▲), [Lys$^{B28}$, Pro$^{B29}$]-insulin (♦, Humalog®), IGF-1 (○) and wild-type human insulin (solid line) to the insulin-like growth factor receptor (IGFR) over a range of peptide concentrations.
Figure 5D:
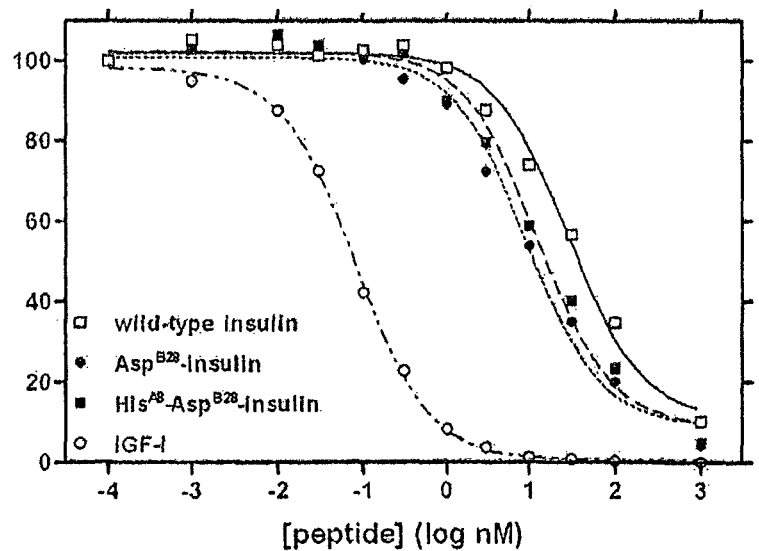
FIG. 5D is a graph of the results of a receptor-binding assay showing the specific binding of His$^{A8}$-[Asp$^{B28}$]-insulin (■) relative to [Asp$^{B28}$] (●, Novalog®), IGF-1 (○) and wild-type human insulin (solid line) to the insulin-like growth factor receptor (IGFR) over a range of peptide concentrations.

Receptor binding data was collected for His[48]-containing insulin analogues at various concentrations of Human Insulin Receptor. FIG. 5A shows the affinity of His[48]-[Lys$^{B28}$, Pro$^{B29}$]-insulin analog (▲), [Lys$^{B28}$, Pro$^{B29}$]-insulin (♦, Humalog®) and wild-type human [Asp$^{B28}$]-insulin (solid line) for human insulin receptor. FIG. 5B shows the affinity of His[48]-insulin (■) relative to [Asp$^{B28}$]-insulin (●, Novalog®) and wild-type human insulin (solid line) to the human insulin receptor. FIG. 5C shows the affinity of His[48]-[Lys$^{B28}$, Pro$^{B29}$]-insulin analog (▲), [Lys$^{B28}$, Pro$^{B29}$]-insulin (●, Humalog®), Insulin-like Growth Factor-1 (IGF-1) (○) and wild-type human insulin (solid line) to the insulin-like growth factor receptor (IGFR) over a range of peptide concentrations. FIG. 5D shows the affinity of His[48]-[Asp$^{B28}$]-insulin (■) relative to [Asp$^{B28}$]-insulin (●, Novalog®), IGF-1 (○) and wild-type human insulin (solid line) to the insulin-like growth factor receptor (IGFR).

A porcine insulin analogue with a substitution of methionine at position A8 (A chain=SEQ. ID. NO 12; B-chain=SEQ. ID. NO. 11) was tested for fibrillation and compared to wild type porcine insulin A8 (A chain=SEQ. ID. NO 2; B-chain=SEQ. ID. NO. 11). The fibrillation testing was similar to that described above. Samples were made 60 μM in a deoxygenated buffer consisting of 10 mM Tris-HCl (pH 7.4) and 140 mM NaCl with 0.01% sodium azide to prevent microbial contamination. Samples (in triplicate) were placed in sealed glass vials and placed on an automated tilting table at 37° C. At successive times aliquots were withdrawn and analyzed by a thioflavin T (ThT) fluorescence spectroscopy assay to determine the onset of fibrillation as provided above. The substitution Met[48] increases the lag time for fibrillation of porcine insulin from 6+/−1.4 days to 8+/−0.82 days.

```
                    SEQ. ID. NO. 11 (porcine B-chain)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Ala SEQ. ID. NO. 12 (A-chain, Met48)
Gly-Ile-Val-Glu-Gln-Cys-Cys-Met-Ser-Ile-Cys-Ser- Leu-Tyr-Gln-Leu-Glu-Asn-Tyr-Cys-Asn
```

Based upon the foregoing disclosure, it should now be apparent that the A8-substituted insulin analogues provided herein will provide increased resistance to fibrillation over their corresponding rapid-acting counterparts while maintaining at least the majority of the activity of the insulin. It is, therefore, to be understood that any variations evident fall within the scope of the claimed invention and thus, the selection of specific component elements can be determined without departing from the spirit of the invention herein disclosed and described.

I claim:

1. A composition comprising a vertebrate insulin analogue or a physiologically acceptable salt thereof, containing a first substitution at position A8, wherein the first substitution is a tryptophan substitution or a methionine substitution, and also containing at least one second substitution that provides a decreased lag time for activity compared to a corresponding wild-type vertebrate insulin, wherein the at least one second substitution comprises an aspartic acid substitution at position B28 or a combination of a lysine substitution at position B28 and a proline substitution at position B29, to provide an insulin analogue having an affinity for insulin analogue at least as high as the corresponding vertebrate wild type insulin.

2. The composition of claim 1, wherein the first substitution at position A8 is a methionine substitution.

3. The composition of claim 1, wherein the vertebrate insulin analogue or a physiologically acceptable salt thereof comprises the sequence of SEQ. ID. NO. 7, and Xaa is methionine or tryptophan.

4. The composition of claim 1, wherein the vertebrate insulin analogue or a physiologically acceptable salt thereof comprises the sequence of SEQ.ID. NO. 10.

5. The composition of claim 1, wherein the vertebrate insulin analogue or a physiologically acceptable salt thereof comprises the sequence of SEQ ID NO: 7, and Xaa is methionine or tryptophan.

6. The composition of claim 1, wherein the vertebrate insulin analogue or a physiologically acceptable salt thereof comprises the sequence of SEQ ID NO: 10.

7. The composition of claim 1, wherein the vertebrate insulin analogue or a physiologically acceptable salt thereof comprises the sequences of SEQ ID NOS: 4 and 10.

8. The composition of claim 1, wherein the vertebrate insulin analogue or a physiologically acceptable salt thereof comprises the sequences of SEQ ID NOS: 5 and 10.

9. The composition of claim 1, wherein the vertebrate insulin analogue or a physiologically acceptable salt thereof comprises the sequence of SEQ ID NO: 12.

10. The composition of claim 1, wherein the vertebrate insulin analogue or a physiologically acceptable salt thereof comprises the sequences of SEQ ID NOS: 4 and 12.

11. The composition of claim 1, wherein the vertebrate insulin analogue or a physiologically acceptable salt thereof comprises the sequences of SEQ ID NOS: 5 and 12.

* * * * *

SEQUENCE LISTING

<160> NUMBER OF SEQ ID NOS: 12

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
            85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Artificial
<220> FEATURE:
<223> OTHER INFORMATION: Insulin B-chain analogue

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 5
<211> LENGTH: 30
<212> TYPE: PRT
<213> ORGANISM: Artificial
<220> FEATURE:
<223> OTHER INFORMATION: Insulin B-chain analogue

```
<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Asp Thr
            20                  25                  30

<210> SEQ ID NO 6
<211> LENGTH: 30
<212> TYPE: PRT
<213> ORGANISM: Artificial
<220> FEATURE:
<223> OTHER INFORMATION: Insulin B-chain analogue

<400> SEQUENCE: 6

Phe Val Asn Gln His Leu Cys Gly Ser Asp Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 7
<211> LENGTH: 21
<212> TYPE: PRT
<213> ORGANISM: Artificial
<220> FEATURE:
<223> OTHER INFORMATION: Insulin A-chain analogue
<220> FEATURE:
<221> NAME/KEY: MISC_FEATURE
<222> LOCATION: (8)..(8)
<223> OTHER INFORMATION: Xaa = His, Lys, Arg, Phe, Tyr or Met

<400> SEQUENCE: 7

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 8
<211> LENGTH: 21
<212> TYPE: PRT
<213> ORGANISM: Artificial
<220> FEATURE:
<223> OTHER INFORMATION: Insulin A-chain analogue

<400> SEQUENCE: 8

Gly Ile Val Glu Gln Cys Cys His Ser Ile Cys Ser Leu Tyr Gln Leu
1               5                   10                  15

Glu Asn Tyr Cys Asn
            20

<210> SEQ ID NO 9
<211> LENGTH: 21
<212> TYPE: PRT
<213> ORGANISM: Artificial
<220> FEATURE:
<223> OTHER INFORMATION: Insulin A-chain analogue

<400> SEQUENCE: 9

Gly Ile Val Glu Gln Cys Cys Lys Ser Ile Cys Ser Leu Tyr Gln Leu
1               5                   10                  15

Glu Asn Tyr Cys Asn
            20

<210> SEQ ID NO 10
```

```
<211> LENGTH: 21
<212> TYPE: PRT
<213> ORGANISM: Artificial
<220> FEATURE:
<223> OTHER INFORMATION: Insulin A-chain analogue

<400> SEQUENCE: 10

Gly Ile Val Glu Gln Cys Cys Trp Ser Ile Cys Ser Leu Tyr Gln Leu
1               5                   10                  15

Glu Asn Tyr Cys Asn
            20

<210> SEQ ID NO 11
<211> LENGTH: 30
<212> TYPE: PRT
<213> ORGANISM: Sus domestica

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 12
<211> LENGTH: 21
<212> TYPE: PRT
<213> ORGANISM: Artificial
<220> FEATURE:
<223> OTHER INFORMATION: Insulin A-chain analogue

<400> SEQUENCE: 12

Gly Ile Val Glu Gln Cys Cys Met Ser Ile Cys Ser Leu Tyr Gln Leu
1               5                   10                  15

Glu Asn Tyr Cys Asn
            20
```